(12) United States Patent
Choi et al.

(10) Patent No.: US 12,324,643 B2
(45) Date of Patent: Jun. 10, 2025

(54) METHOD AND SYSTEM FOR MITIGATING COLLISION OF SURGICAL ROBOT

(71) Applicant: MEERE COMPANY INC., Hwaseong-si (KR)

(72) Inventors: Jong Do Choi, Suwon-si (KR); Tae Won Kim, Gunpo-si (KR)

(73) Assignee: Meere Company Inc., Hwaseong-si (KR)

( * ) Notice: Subject to any disclaimer, the term of this patent is extended or adjusted under 35 U.S.C. 154(b) by 1035 days.

(21) Appl. No.: 17/413,263

(22) PCT Filed: Nov. 1, 2019

(86) PCT No.: PCT/KR2019/014697
§ 371 (c)(1),
(2) Date: Jun. 11, 2021

(87) PCT Pub. No.: WO2020/122416
PCT Pub. Date: Jun. 18, 2020

(65) Prior Publication Data
US 2022/0047345 A1 Feb. 17, 2022

(30) Foreign Application Priority Data

Dec. 13, 2018 (KR) .................. 10-2018-0161177

(51) Int. Cl.
*A61B 34/37* (2016.01)
*B25J 9/16* (2006.01)
(Continued)

(52) U.S. Cl.
CPC ............ *A61B 34/37* (2016.02); *B25J 9/1666* (2013.01); *B25J 9/1676* (2013.01); *B25J 13/085* (2013.01);
(Continued)

(58) Field of Classification Search
CPC ... A61B 34/37; A61B 2090/066; A61B 34/30; A61B 2090/065; A61B 90/37;
(Continued)

(56) References Cited

U.S. PATENT DOCUMENTS

2007/0120512 A1* 5/2007 Albu-Schaffer ....... B25J 9/1643
318/568.2
2009/0248038 A1 10/2009 Blumenkranz et al.
(Continued)

FOREIGN PATENT DOCUMENTS

CN 104985598 A 10/2015
CN 107848126 A 3/2018
(Continued)

OTHER PUBLICATIONS

International Search Report and Written Opinion mailed Feb. 6, 2020 in international Application No. PCT/KR2019/014697, in 10 pages. (English translation of ISR in 2 pages.).
(Continued)

*Primary Examiner* — Bao Long T Nguyen
(74) *Attorney, Agent, or Firm* — Knobbe, Martens, Olson & Bear, LLP (57) ABSTRACT

This application relates to a method of mitigating a collision of a slave robot for surgery. In one aspect, the method includes obtaining an external torque generated when the slave robot collides with another object or a person and obtaining a joint angle of the slave robot. The method may also include calculating a target joint angle for changing a position of the slave robot based on the obtained external torque and the obtained joint angle, such that the external torque is attenuated. The method may further include controlling the slave robot to change the position thereof from the obtained joint angle to the calculated target joint angle.

10 Claims, 10 Drawing Sheets

(51) Int. Cl.
*B25J 13/08* (2006.01)
*B25J 19/06* (2006.01)
*A61B 90/00* (2016.01)

(52) U.S. Cl.
CPC ......... *B25J 19/06* (2013.01); *A61B 2090/066* (2016.02); *B25J 13/088* (2013.01)

(58) Field of Classification Search
CPC ........... A61B 2017/00119; A61B 2017/00128; A61B 2034/2059; A61B 2090/067; A61B 2090/0811; A61B 90/00; A61B 34/74; A61B 34/76; A61B 90/03; A61B 2017/00212; B25J 9/1666; B25J 9/1676; B25J 13/085; B25J 19/06; B25J 13/088; B25J 9/1633; B25J 9/1641; B25J 9/1689; B25J 9/1692; B25J 19/02; G05B 2219/37624; G05B 2219/37632; G05B 2219/40184
See application file for complete search history.

(56) References Cited

U.S. PATENT DOCUMENTS

| | | | |
|---|---|---|---|
| 2014/0052154 A1 | 2/2014 | Griffiths et al. | |
| 2017/0106541 A1 | 4/2017 | Naitou et al. | |
| 2017/0128136 A1* | 5/2017 | Post | A61B 34/30 |
| 2017/0367774 A1* | 12/2017 | Scholan | B25J 9/1689 |
| 2018/0079090 A1 | 3/2018 | Koenig et al. | |
| 2019/0022857 A1* | 1/2019 | Conus | B25J 9/0006 |
| 2019/0184576 A1* | 6/2019 | Smith | B25J 13/087 |

FOREIGN PATENT DOCUMENTS

| | | | |
|---|---|---|---|
| CN | 108748158 A | 11/2018 | |
| EP | 3 369 536 A1 | 9/2018 | |
| JP | 2001353687 A | 12/2001 | |
| JP | 2006116650 A | 5/2006 | |
| JP | 2011517419 A | 6/2011 | |
| JP | 2013169609 A | 9/2013 | |
| JP | 2017177255 A | 10/2017 | |
| KR | 10-2018-0067652 A | 6/2018 | |
| KR | 20180067652 A | 6/2018 | |
| WO | WO 2016/071674 A1 | 5/2016 | |
| WO | WO 2017/169097 A1 | 10/2017 | |
| WO | WO 2017/169098 A1 | 10/2017 | |
| WO | WO 2017/214243 A1 | 12/2017 | |

OTHER PUBLICATIONS

Communication pursuant to Article 94(3) EPC in European Application No. 19897325.7 Jun. 12, 2024.

Extended European Search Report received in European Application No. 19897325.7 dated Jan. 26, 2022.

Kim et al., "Safe joint module for safe robot arm based on passive active compliance method," Mechatronics, 22, pp. 1023-1030, 2012.

Notice of Allowance received in Chinese Application No. 201980082222.3 dated Dec. 29, 2023.

Office Action received in Chinese Application No. 201980082222.3 dated Jun. 15, 2023.

Osa et al., "Hybrid Rate-Admittance Control With Force Reflection for Safe Teleoperated Surgery," IEEE/ASME Transactions on Mechatronics, vol. 20, No. 5, pp. 2379-2390, 2015.

Ramadan "Rototic solutions to facilitate studying human motor control," 14$^{th}$ International Conference on Ubiquitous Robots and Ambient Intelligence, 2017, pp. 1-10.

* cited by examiner

METHOD AND SYSTEM FOR MITIGATING COLLISION OF SURGICAL ROBOT

The present application is a U.S. national phase application under 35 U.S.C. § 371 of International Application No. PCT/KR2019/014697, filed on Nov. 1, 2019, which claims the benefit of Korean Patent Application No. 10-2018-0161177 filed on Dec. 13, 2018, in the Korean Intellectual Property Office, the entire disclosure of each of which is incorporated herein by reference.

TECHNICAL FIELD

The present disclosure relates to a method and system for controlling a surgical robot so as to mitigate collisions when the surgical robot collides with another object or a person.

BACKGROUND ART

Surgery denotes a process of curing illness by cutting, incising, or manipulating the skin, the mucosa layer, and other tissues by using a medical machine. In particular, laparotomy that treats, shapes, or removes an organ by cutting and opening the skin of a surgical site may cause bleeding, side effects, pain of a patient, scar, etc., and thus, surgery performed by a robot has been recently highlighted as an alternative.

Such a surgical robot may be classified into a master robot that generates and transmits a necessary signal by manipulation of an operator, and a slave robot that receives signals from a manipulator and directly applies necessary operations to the patient. The master robot and the slave robot may be divided as parts of one surgical robot, or may be configured as separate devices and arranged in an operating room.

The master robot is equipped with a device for manipulation of an operator, in the case of a robot surgery, the operator does not directly manipulate a surgical tool, but manipulates the device to make various surgical tools installed on the slave robot perform operations required for surgery.

In addition, the operator may manipulate the device while watching images captured by the surgical tool and displayed on a display member. In this case, a field of view of the operator may be concentrated on the display member, and thus, the operator may not identify the position of the slave robot. Moreover, the operator may not recognize that a situation in which the slave robot collides with another object, the patient, a surgical assistant, etc. has occurred. When the operator does not recognize the collision situation and continues to manipulate the device, the slave robot may be overwhelmed or the patient may be injured.

Accordingly, when the slave robot collides with another object or a person, a method of controlling the slave robot to mitigate the collision is being demanded.

DESCRIPTION OF EMBODIMENTS

Technical Problem

Provided are a method and system for controlling a movement of a surgical slave robot so as to mitigate a collision when the surgical slave robot collides with another object or a person.

The solutions of the present disclosure are not limited to the aforementioned solutions, and other solutions of the present disclosure may be understood by the following description and will become apparent from the embodiments of the present disclosure.

Solution to Problem

According to an embodiment, a method of mitigating a collision of a slave robot for surgery includes: a first step for obtaining an external torque generated when the slave robot collides with another object or a person; a second step for obtaining a joint angle of the slave robot; a third step for calculating a target joint angle for changing a position of the slave robot based on the obtained external torque and the obtained joint angle, such that the external torque is attenuated; and a fourth step for controlling the slave robot to change the position thereof from the obtained joint angle to the calculated target joint angle.

Advantageous Effects of Disclosure

Damage to a slave robot or another object or damage to human beings may be restrained by controlling collision of the slave robot to be mitigated. In addition, by notifying an operator of the collision situation of the slave robot, the operator may be prevented from forcibly driving the slave robot.

The effects according to the present disclosure are not limited by the aforementioned effects described above, and more various effects are included in the present specification.

BRIEF DESCRIPTION OF DRAWINGS

FIGS. 4A to 6B are diagrams illustrating experimental results in which collision of the slave robot is mitigated according to a method of mitigating the collision of the slave robot according to an embodiment.

BEST MODE

According to an embodiment, a method of mitigating a collision of a slave robot for surgery includes: a first step for obtaining an external torque generated when the slave robot collides with another object or a person; a second step for obtaining a joint angle of the slave robot; a third step for calculating a target joint angle for changing a position of the slave robot based on the obtained external torque and the obtained joint angle, such that the external torque is attenuated; and a fourth step for controlling the slave robot to change the position thereof from the obtained joint angle to the calculated target joint angle.

In the above method, the first step may include: measuring, by a torque sensor, a torque of a motor installed in the slave robot; and calculating the external torque from the measured torque of the motor.

In the above method, the first step may include: measuring, by a current sensor, a current flowing through the motor installed in the slave robot; and calculating the external torque from the measured current value.

In the above method, the calculating of the external torque from the measured current value may include: calculating the torque of the motor from the measured current value; calculating a gravity compensation torque for compensating for a gravity applied to the slave robot; and calculating the external torque based on the calculated torque of the motor and the calculated gravity compensation torque.

In the above method, the target joint angle may be calculated by a linear combination of the obtained external torque and the obtained joint angle.

The above method may further include outputting an alarm to notify an operator of the slave robot colliding with another object or person.

In the above method, the alarm may include at least one selected from a visual alarm, an audible alarm, and a tactile alarm.

The above method may further include: a fifth step for comparing the obtained external torque with a reference value; repeatedly performing the first step to the fifth step, when the obtained external torque is equal to or greater than the reference value; measuring a period in which the first step to the fifth step are repeatedly performed; and controlling the slave robot not to move when the measured period is equal to or longer than a preset period.

In the above method, the slave robot may be remotely controlled according to a command of an operator, which is input through a master console.

According to another embodiment, a robot system for surgery includes: a master console operated by an operator; a slave robot moved based on a manipulation on the master console; and at least one processor configured to control a movement of the slave robot such that a collision between the slave robot and another object or person is buffered, wherein the at least one processor is configured to execute: a first step for obtaining an external torque that is generated when the slave robot collides with another object or person; a second step for obtaining a joint angle of the slave robot; a third step for calculating a target joint angle for changing a position of the slave robot based on the obtained external torque and the obtained joint angle, such that the external torque is attenuated; and a fourth step for controlling the slave robot to change the position thereof from the obtained joint angle to the calculated target joint angle.

Mode of Disclosure

Hereinafter, one or more embodiments of the disclosure will be described in detail with reference to accompanying drawings. The description provided below is only for specifying embodiments and does not limit or restrict the scope of the invention. Things that one of ordinary skill in the art may easily infer from the following detailed description and examples are interpreted to fall within the scope of the disclosure.

The terms "consist(s) of" or "include(s) (or comprise(s))" should not be interpreted or understood as including, without exception, all of the plurality of elements or the plurality of steps disclosed in the description. In other words, it should be understood that some of the elements or some of the steps may not be included, or that additional elements or steps may be further included.

The terms used herein are general terms that are currently widely used while considering functions in the present disclosure, but the terms may have different meanings according to an intention of one of ordinary skill in the art, precedent cases, or the appearance of new technologies. Also, some terms may be arbitrarily selected by the applicant. In this case, the meaning of the selected terms will be described in the detailed description. Thus, the terms used herein have to be defined based on the meaning of the terms together with the description throughout the specification.

Figure 1:
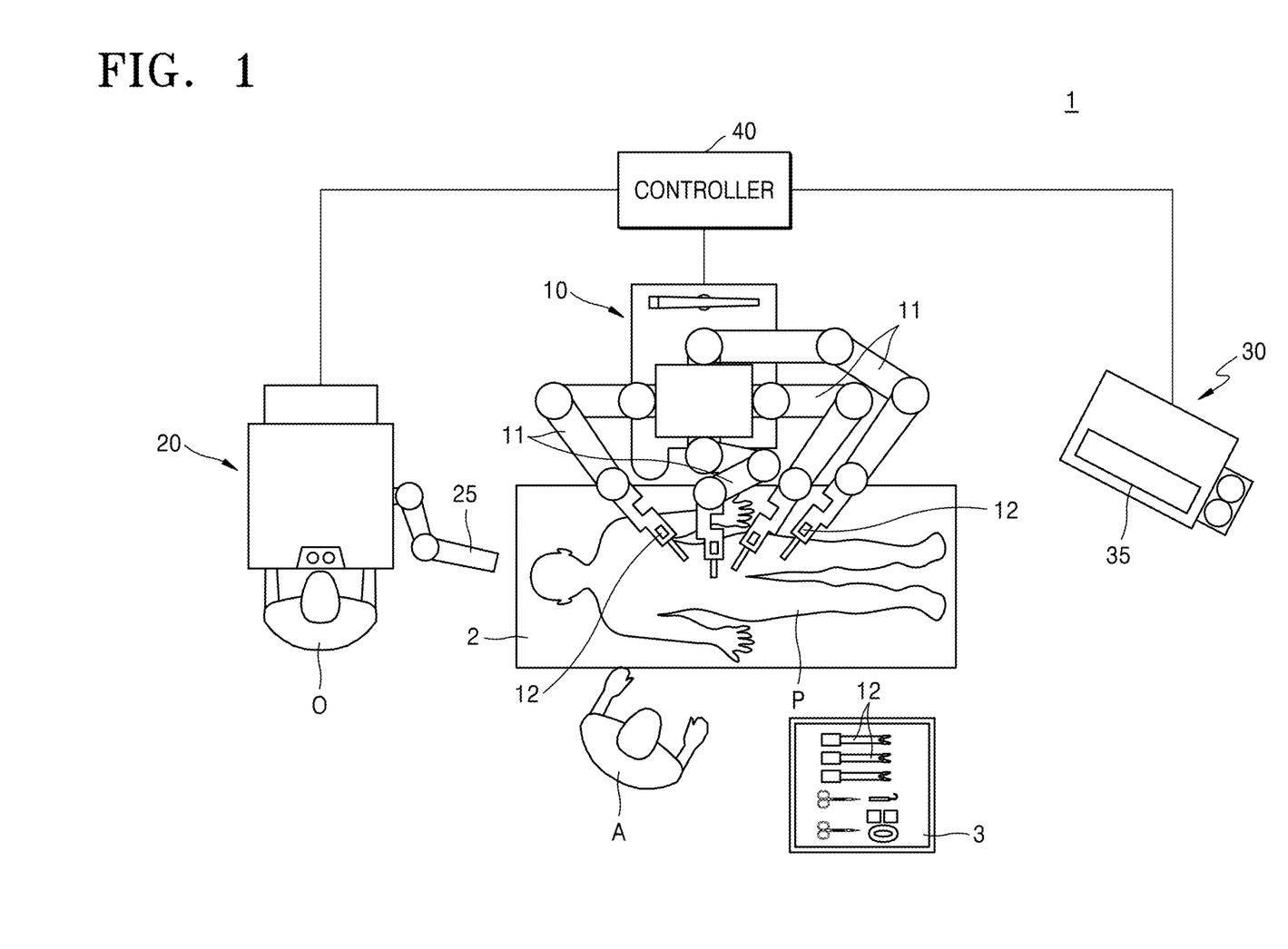
FIG. 1 is a plan view of a surgical robot system according to an embodiment.

FIG. 1 is a plan view of a surgical robot system according to an embodiment.

Referring to FIG. 1, a surgical robot system 1 according to an embodiment includes a slave robot 10 performing surgery on a patient P lying on an operating table 2, and a master console 20 allowing an operator O to remotely control the slave robot 10. In addition, the surgical robot system 1 may include a vision cart 30. Through a display unit 35 of the vision cart 30, the assistant A may check the progress of the surgery.

The slave robot 10 may include at least one slave arm 11. In general, a slave arm has a similar function to that of an arm and/or a wrist of a human being, and denotes a device having a wrist to which a certain tool may be attached. In the specification herein, the slave arm 11 may be defined as a concept encompassing such elements as an upper arm, a lower arm, a wrist, and an elbow, and a surgical instrument coupled to the wrist, etc. The slave arm 11 of the slave robot 10 as above may be implemented to operate with multiple degrees of freedom. The slave arm 11 includes, for example, a surgical instrument inserted into a surgical site of the patient P, a transport driving unit that moves the surgical instrument in a lengthwise direction, a rotation driving unit that rotates the surgical instrument, and a surgical instrument driving unit installed at an end of the surgical instrument, for incising or cutting the lesion. However, the composition of the slave arm 11 is not limited thereto, and it is to be appreciated that such an example does not limit the scope of claims of the present disclosure.

One or more slave robots 10 may be used to perform surgery on the patient P, and a surgical tool 12 for displaying an image of a surgical site through a display member (not shown) may be implemented as an independent slave robot 10.

Also, as described above, the embodiments of the present disclosure may be universally used in surgeries in which various surgical endoscopes (e.g., thoracoscopy, arthroscopy, parenteral, etc.) other than laparoscopy are used.

The master console 20 and the slave robot 10 are not necessarily provided as separate devices that are physically separated from each other, and may be combined and implemented integrally with each other.

The master console 20 includes a master arm (not shown) and a display member (not shown). Also, the master console 20 may additionally include an external display apparatus 25 for displaying the status of the operator O.

In detail, the master console 20 includes a master arm that the operator O may operate. When the operator O manipulates the master arm, a manipulation signal is transmitted to the slave robot 10 through a wired or wireless communication network to control the slave arm 11 is controlled. That is, surgical operations such as moving of a location, rotation, cut operation, etc. of the slave arm 11 may be performed by the operator O manipulating the master arm.

For example, the operator O may manipulate the slave arm 11 or the surgical tool 12 by using a manipulation lever of a handle type. The manipulation lever as above may have various mechanical configurations according to the manipulation method thereof and may be provided in various types, for example, a master handle for manipulating operations of the slave arm 11 or the surgical tool 12, and various input units such as a joystick, a keypad, a trackball, or a touch-screen added to the master console 20 for manipulating functions of entire system, for operating the slave arm 11 of the slave robot 10 and/or other surgical instruments.

An image captured by the surgical tool 12 is displayed as an image on the display member of the master console 20. Also, the display member may display a certain virtual manipulation plate independently or along with the image captured by the surgical tool 12.

The display member may be provided in various types by which the operator O may check the image. For example, the display apparatus may be provided to correspond to both eyes of the operator O. In another example, the display member may include one or more monitors such that information that is necessary during the surgery may be displayed on each monitor. The number of the display members may be determined depending on the type or kind of the information that needs to be displayed.

The vision cart 30 is installed to be spaced apart from the slave robot 10 or the master console 20, and the progress of the surgery may be checked from the outside through the display unit 35.

The image displayed on the display unit 35 may be the same as the image displayed on the display member of the operator O. The assistant A may assist the surgery performed by the operator O while checking the image on the display unit 35. For example, the assistant A may replace the surgical tool 12 from an instrument cart 3 according to the progress of the surgery.

A central controller 40 is connected to the slave robot 10, the master console 20, and the vision cart 30 to receive/transmit signals from/to each of the slave robot 10, the master console 20, and the vision cart 30.

The central controller 40 includes at least one processor that controls the slave robot 10 to move based on the operator O manipulating the master console 20. The at least one processor may be implemented as an array of a plurality of logic gates, or as a combination of a universal microprocessor and a memory storing programs that may be executed in the microprocessor.

The least one processor may control the slave robot 10 so that the collision is alleviated when the slave robot 10 collides with another object, the patient P, the operator O, etc. Hereinafter, a method of controlling the movement of the slave robot 10 such that the collision of the slave robot 10 with another object or another person may be mitigated will be described with reference to FIGS. 2 to 7.

Figure 2:
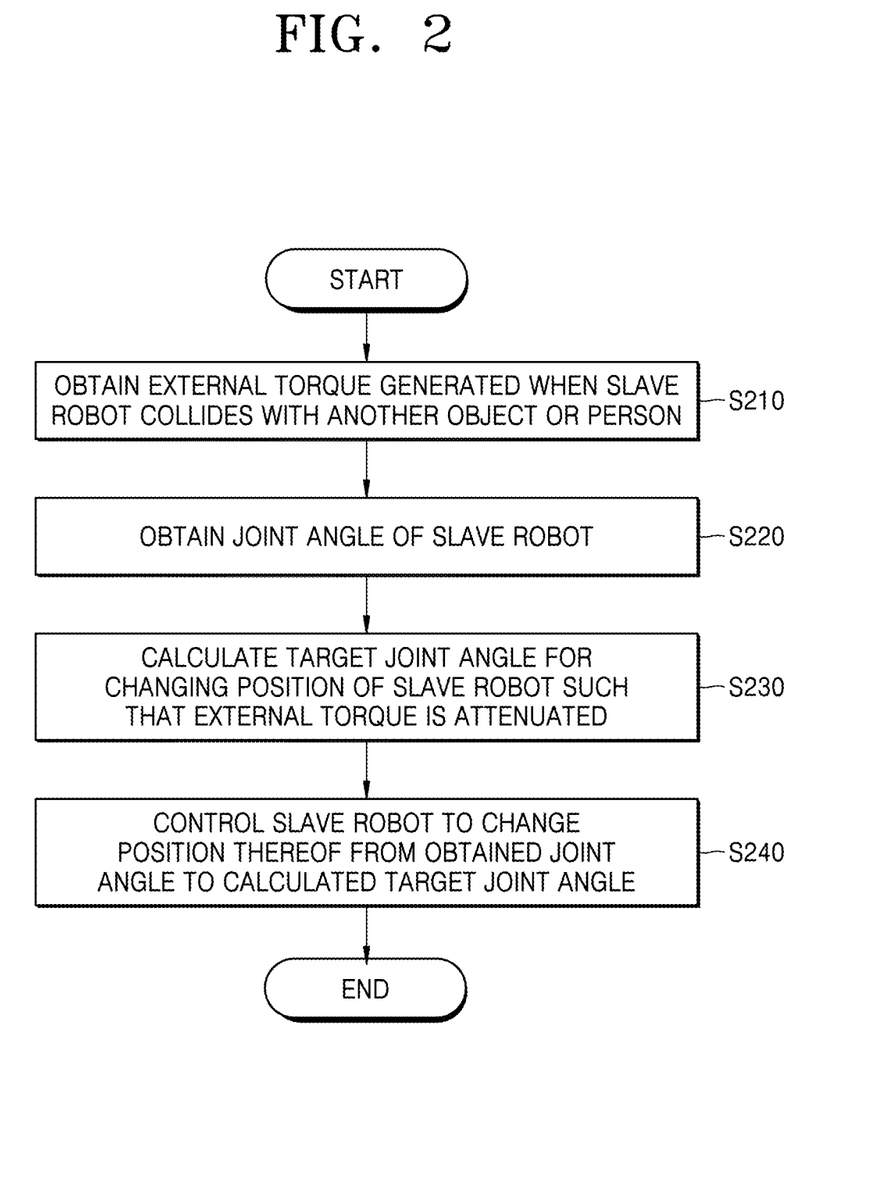
FIG. 2 is a flowchart illustrating a method of mitigating a collision of a slave robot according to an embodiment.
Figure 3:
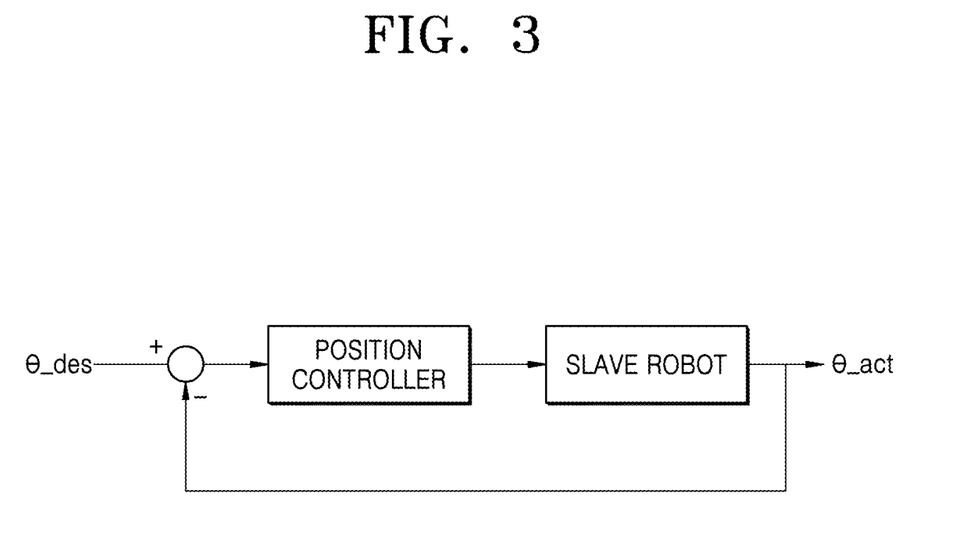
FIG. 3 is a diagram showing an example of a position controller.

FIG. 2 is a flowchart illustrating a method of mitigating a collision of a slave robot according to an embodiment.

In operation S210, at least one processor may acquire an external torque that occurs when the slave robot collides with another object or person.

The slave arm of the slave robot may include a link and a joint, and the joint may include a motor to rotate the link.

A torque $\tau\_act$ output by the motor of the slave robot may be expressed by Equation 1 below.

$$\tau\_act = \tau\_acc + \tau\_vel + \tau\_fric + \tau\_grav + \tau\_extern \quad \text{(Equation 1)}$$

Here, $\tau\_acc$ denotes a torque according to an acceleration of the motor, $\tau\_vel$ denotes a torque according to a speed of the motor, $\tau\_fric$ denotes a torque according to a frictional force applying to the motor, $\tau\_grav$ denotes a gravity compensation torque for compensating for a gravity applying to the motor, and $\tau\_extern$ denotes a torque according to an external force applied to the motor. The torque generated when the slave robot collides with another object or person corresponds to the external torque $\tau\_extern$.

When the motor is driven at a low-speed state, Equation 1 above may be expressed as Equation 2 below.

$$\tau\_act = \tau\_grav + \tau\_extern \quad \text{(Equation 2)}$$

At least one processor may obtain the torque $\tau\_act$ of the motor. The at least one processor may indirectly obtain the torque $\tau\_act$ of the motor through a current measurement method, or may directly obtain the torque $\tau\_act$ of the motor through a torque measurement method.

For example, at least one processor may calculate the torque $\tau\_act$ of the motor from a measurement value of a current flowing through the motor. The current flowing through the motor may be measured by a current sensor. For example, a current value may be measured by dividing a voltage value applied to a resistor mounted on a motor by a resistance value. When the value of the current flowing through the motor is measured, the at least one processor may obtain the torque $\tau\_act$ of the motor from the measured current value by using a proportionality between the torque $\tau\_act$ of the motor and the current of the motor. As described above, the torque $\tau\_act$ of the motor obtained through estimation by the current sensor may be used in the form of admittance control.

In another example, the at least one processor may obtain the torque $\tau\_act$ of the motor from a sensing value measured by the torque sensor. The torque sensor may be a sensor that measures three-axis forces (Fx, Fy, Fz) and three-axis moments (Mx, My, Mz) applied to the motor. In addition, the torque sensor may be a strain gauge type sensor, an optical sensor, etc., but is not limited thereto. As described above, the torque $\tau\_act$ of the motor obtained via the torque sensor may be used in the form of impedance control type.

The at least one processor may obtain a gravity compensation torque $\tau\_grav$ for compensating for the gravity applied to the motor.

For example, the at least one processor may calculate a gravity compensation current from the position of the slave robot, and calculate the gravity compensation torque $\tau\_grav$ from the calculated gravity compensation current.

The at least one processor may obtain the external torque $\tau\_extern$ based on the obtained torque $\tau\_act$ of the motor and the gravity compensation torque $\tau\_grav$.

For example, at least one processor may calculate the external torque $\tau\_extern$ by using Equation 3 below, which is obtained by modifying Equation 2 above.

$$\tau\_extern = \tau\_act - \tau\_grav \quad \text{(Equation 3)}$$

In operation S220, the at least one processor may obtain a joint angle $\theta\_act$ of the slave robot. In detail, the at least one processor may obtain the joint angle $\theta\_act$ of the slave arm of the slave robot.

For example, the at least one processor may obtain the joint angle $\theta\_act$ of the slave arm from a value measured by an encoder. Various types of encoders such as an incremental encoder, an absolute encoder, a magnetic encoder, a potentiometer, etc. may be used for detecting the joint angle.

In operation S230, the at least one processor may calculate a target joint angle $\theta\_des$ for changing the position of the slave robot such that the external torque $\tau\_extern$ may be attenuated, based on the obtained external torque $\tau\_extern$ and the obtained joint angle $\theta\_act$.

For example, the at least one processor may set a state equation of the slave robot as in Equation 4 below.

$$\tau\_extern = Md*\ddot{\theta}\_err + Bd*\dot{\theta}\_err + Kd*\theta\_err \quad \text{(Equation 4)}$$

Here, $\theta\_err$ is $\theta\_des - \theta\_act$, Md denotes an inertia matrix, Bd denotes a viscous matrix, and Kd denotes a stiffness matrix.

In order to perform a stiffness control, the at least one processor may set the state equation represented by Equation 4 above as in Equation 5 below.

$$\tau\_extern = Kd(\theta\_des - \theta\_act) \quad \text{(Equation 5)}$$

Equation 5 above may be summarized as in Equation 6 below, and the at least one processor may calculate the target joint angle θ_des by using Equation 6 below.

$$\theta\_des = \theta\_act + (\tau\_extern)/Kd \quad \text{(Equation 6)}$$

In operation S240, the at least one processor may control the slave robot to change the position thereof to the calculated target joint angle θ_des from the obtained joint angle θ_act.

For example, the at least one processor may set a reference joint angle that the slave robot wants to follow as the target joint angle θ_des, and may set the target joint angle θ_des as an input value of a position controller. For example, the target joint angle θ_des may be input to the position controller shown in FIG. 3.

Also, the at least one processor may output an alarm for notifying the operator that the slave robot collides with another object or person. The alarm includes at least one of a visual alarm, an audible alarm, and a tactile alarm.

For example, the alarm may be displayed on the display member of the master console (see 20 of FIG. 1). The operator may recognize that the slave robot collides with another object or person through the display of an alarm on the display member, while watching the image displayed on the display member and performing the surgery.

In another example, the alarm may be transmitted to the operator in the form of vibration of the manipulation lever of the master console (see 20 of FIG. 1). The operator controls the slave robot via the manipulation lever, and then, may recognize that the slave robot collides with another object or person through vibration of the manipulation lever.

In another example, the alarm may be displayed on the display unit (see 35 of FIG. 1) of the vision cart. The assistant (see A of FIG. 1) may recognize that the slave robot collides with another object or person through an alarm displayed on the display unit.

By notifying the operator or the assistant of the collision situation of the slave robot through an alarm, the operator may be prevented from excessively manipulating the slave robot.

The at least one processor may compare a reference value set in advance with the external torque τ_extern.

The at least one processor may continue to output the alarm until the external torque τ_extern is equal to or less than the reference value. The operator may recognize that the slave robot is still causing a collision with another object or person through a continuously ringing alarm.

The at least one processor may repeatedly perform operations S210 to S240 when the external torque τ_extern is equal to or greater than the reference value. In addition, the at least one processor may control the slave robot not to move when a period of repeatedly performing operations S210 to S240 is longer than a preset period. When the external torque τ_extern is equal to or greater than the reference value for a preset period or longer, it suggests that the slave robot is still colliding with another object or person, and thus, the at least one processor forcibly controls the slave robot not to move such that damage to the slave robot or another object or damage to human beings may be prevented.

FIGS. 4A to 6B are diagrams illustrating experimental results in which collision of the slave robot is mitigated according to a method of mitigating the collision of the slave robot according to the above embodiment.

Figure 4A:
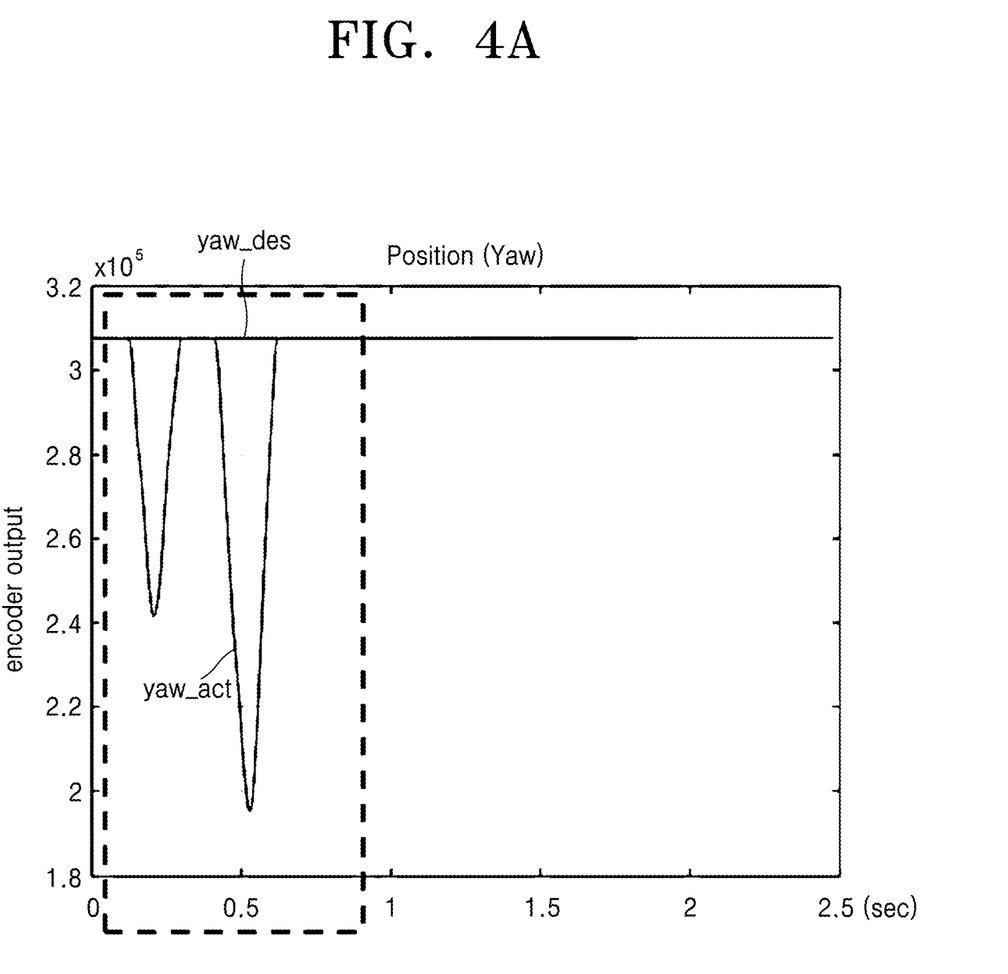
Figure 4B:
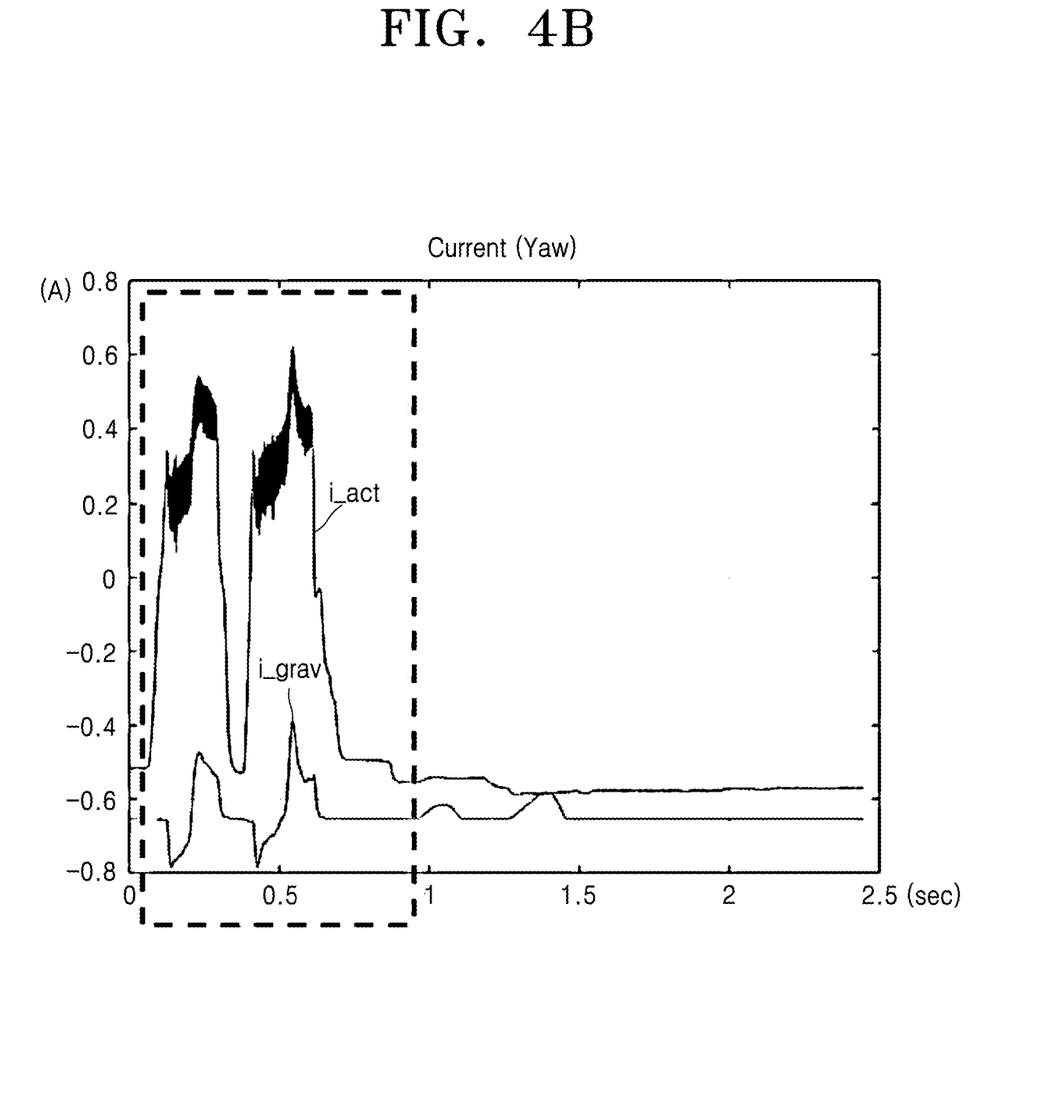

FIGS. 4A and 4B show experimental results when an external force is applied to a yaw-axis position of the slave robot. FIG. 4A shows an output of an encoder measuring a yaw-axis angle of the motor of the slave robot, and FIG. 4B shows a current flowing through the motor of the slave robot.

Referring to FIGS. 4A and 4B, it may be recognized that, as the external force is applied in a range from about 0 second to about 0.7 second, a yaw-axis angle yaw_act of the motor of the slave robot deviates from a target yaw-axis angle yaw_des. In addition, it is recognized that a difference between the current i_act flowing through the motor and a current i_grav due to the gravity increases. Because the current i_act flowing through the motor represents the motor torque τ_act and the current i_grav due to the gravity represents the gravity compensation torque τ_grav, the increase in the difference between the current i_act flowing through the motor and the current i_grav due to the gravity denotes that the external torque τ_extern increases.

The at least one processor controls the slave robot to change the position thereof to the target yaw-axis angle yaw_des according to operations S210 to S240 described above. According to the result, the yaw-axis angle yaw_act of the motor is similar to the target yaw-axis angle yaw_des in a section after about 0.7 second in FIG. 4A. In addition, it may be recognized that the difference between the current i_act flowing through the motor and the current i_grav due to the gravity in the section after about 0.7 seconds of FIG. 4B has decreased within a certain range.

Figure 5A:
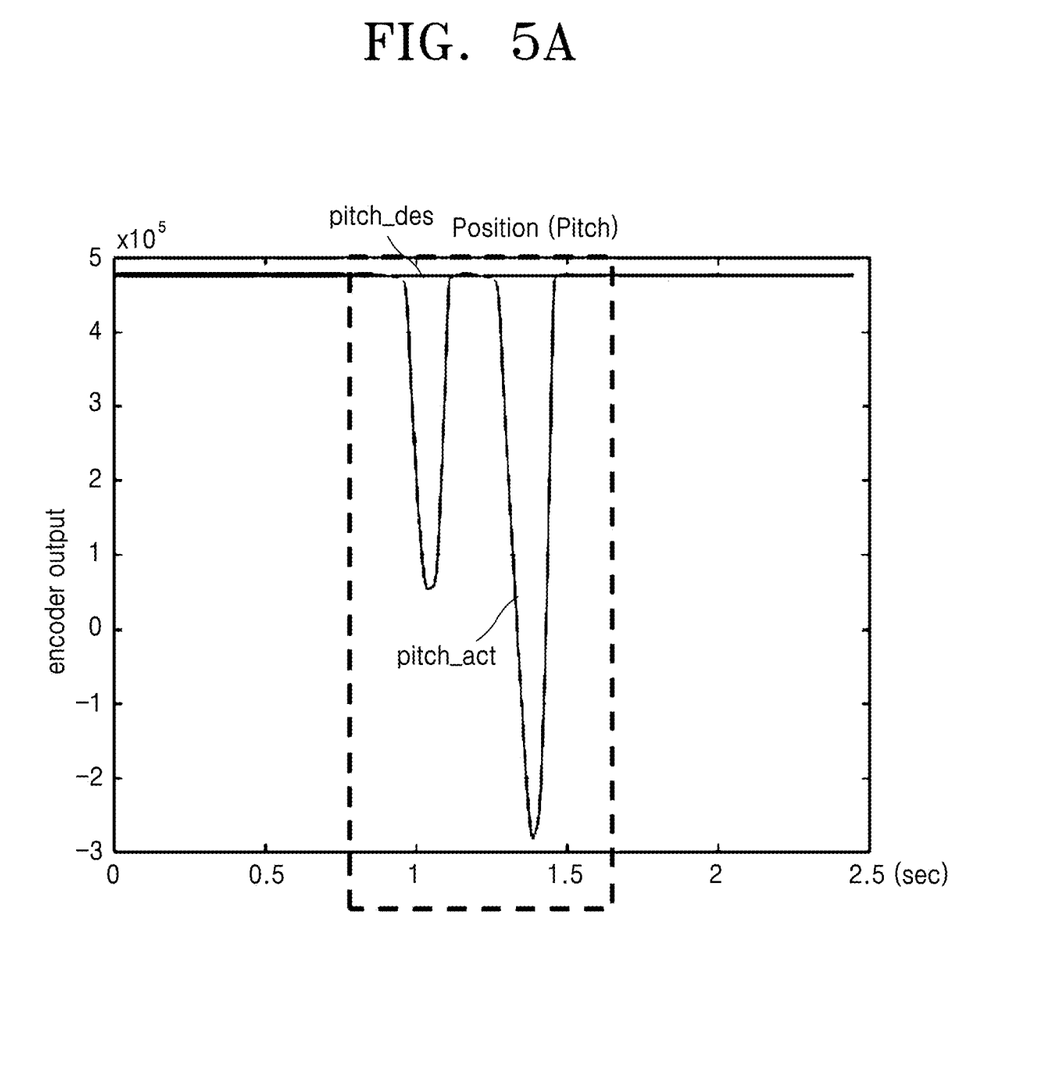
Figure 5B:
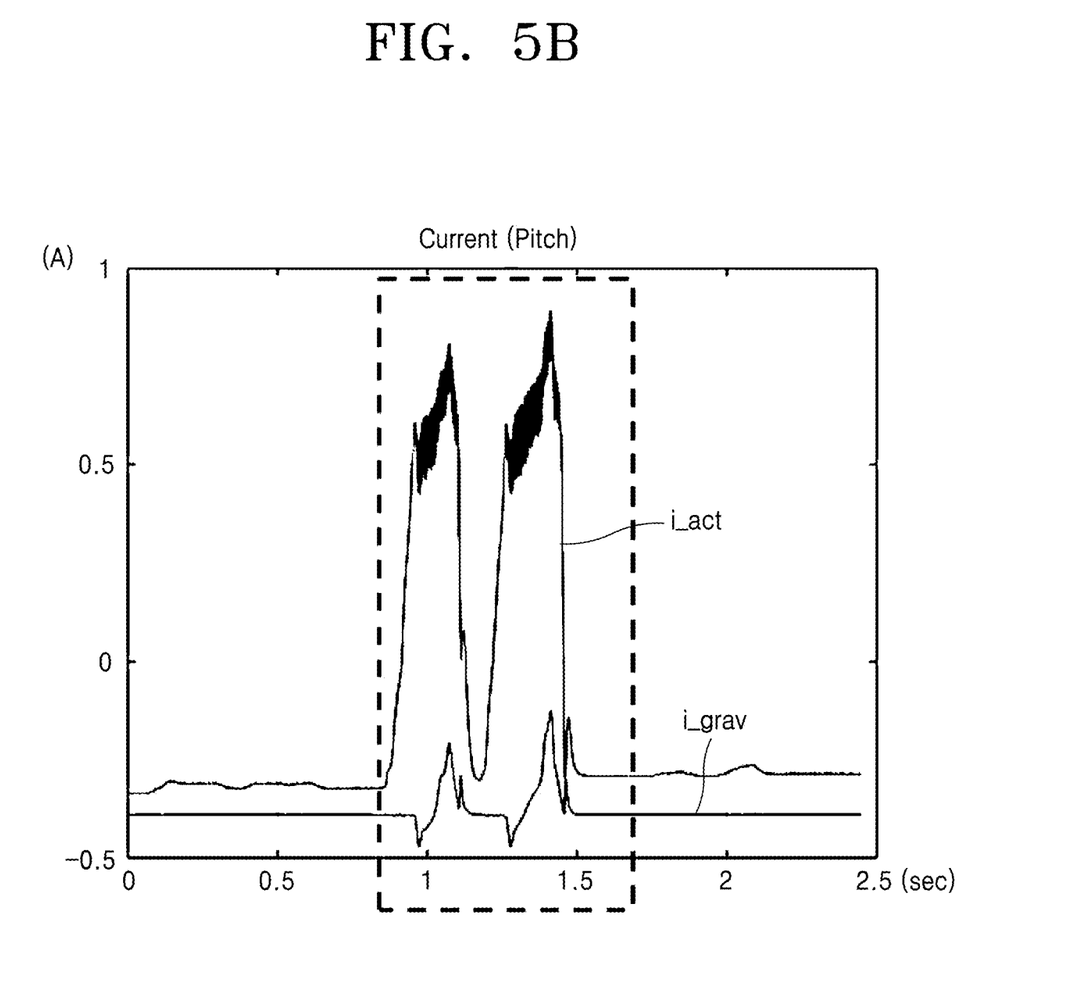

Next, FIGS. 5A and 5B show experimental results for a case in which an external force is applied to the position of the slave robot in a pitch-axis. FIG. 5A shows an output of the encoder measuring a pitch-axis angle of the motor of the slave robot, and FIG. 5B shows a current flowing through the motor of the slave robot.

Referring to FIGS. 5A and 5B, as an external force is applied between about 1 second and about 1.5 seconds, it may be recognized that the pitch-axis angle pitch_act of the motor of the slave robot deviates from a target pitch-axis angle pitch_des. In addition, it is recognized that a difference between the current i_act flowing through the motor and a current i_grav due to the gravity increases. This denotes that the external torque τ_extern increases.

The at least one processor controls the slave robot to change the position thereof to the target pitch-axis angle pitch_des according to above-described operations S210 to S240. As a result, it may be recognized that the pitch-axis angle pitch_act of the motor is similar to the target pitch-axis angle pitch_des in a section after about 1.5 seconds in FIG. 5A. In addition, it may be recognized that the difference between the current i_act flowing through the motor and the current i_grav due to the gravity in the section after about 1.5 seconds of FIG. 5B has decreased within a certain range.

Figure 6A:
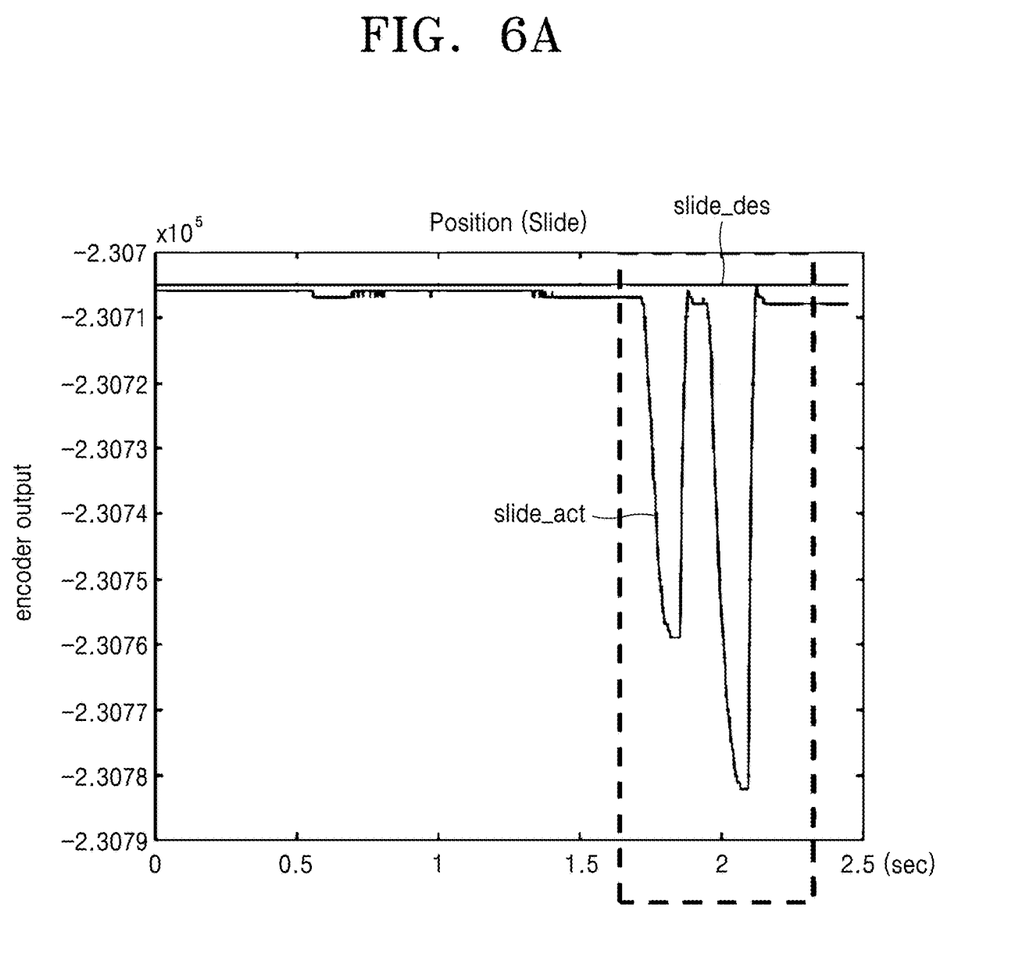
Figure 6B:
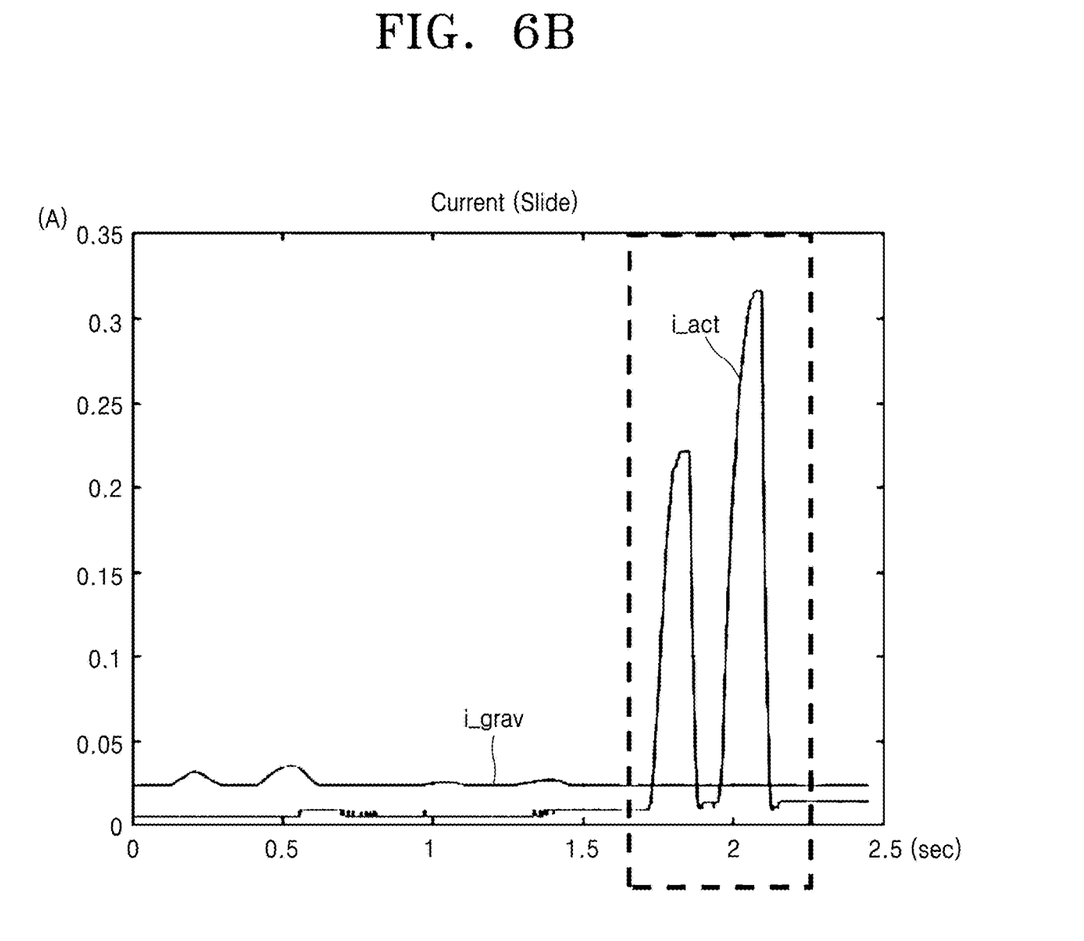

Next, FIGS. 6A and 6B show experimental results for a case in which an external force is applied to a position of the slave robot in a slide-axis direction. FIG. 6A shows an output of the encoder measuring a slide-axis angle of the motor of the slave robot, and FIG. 6B shows a current flowing through the motor of the slave robot.

Referring to FIGS. 6A and 6B, as an external force is applied between about 1.5 seconds to about 2.2 seconds, it may be recognized that the slide-axis angle slide_act of the motor of the slave robot deviates from a target slide-axis angle slide_des. In addition, it is recognized that a difference between the current i_act flowing through the motor and a current i_grav due to the gravity increases. This denotes that the external torque τ_extern increases.

The at least one processor controls the slave robot to change the position thereof to the target slide-axis angle slide_des according to above-described operations S210 to S240. According to the result, it may be recognized that the slide-axis angle slide_act of the motor coincides with the target slide-axis angle slide_des in the section after about 2.2 seconds in FIG. 6A. In addition, it may be recognized that the difference between the current i_act flowing through the motor and the current i_grav due to the gravity in the section after about 2.2 seconds of FIG. 6B has decreased within a certain range.

On the other hand, embodiments of the disclosure described above may be implemented in a general purpose digital computer to be written as a program that may be executed on a computer, and operate the programs using a computer readable recording medium.

Figure 7:
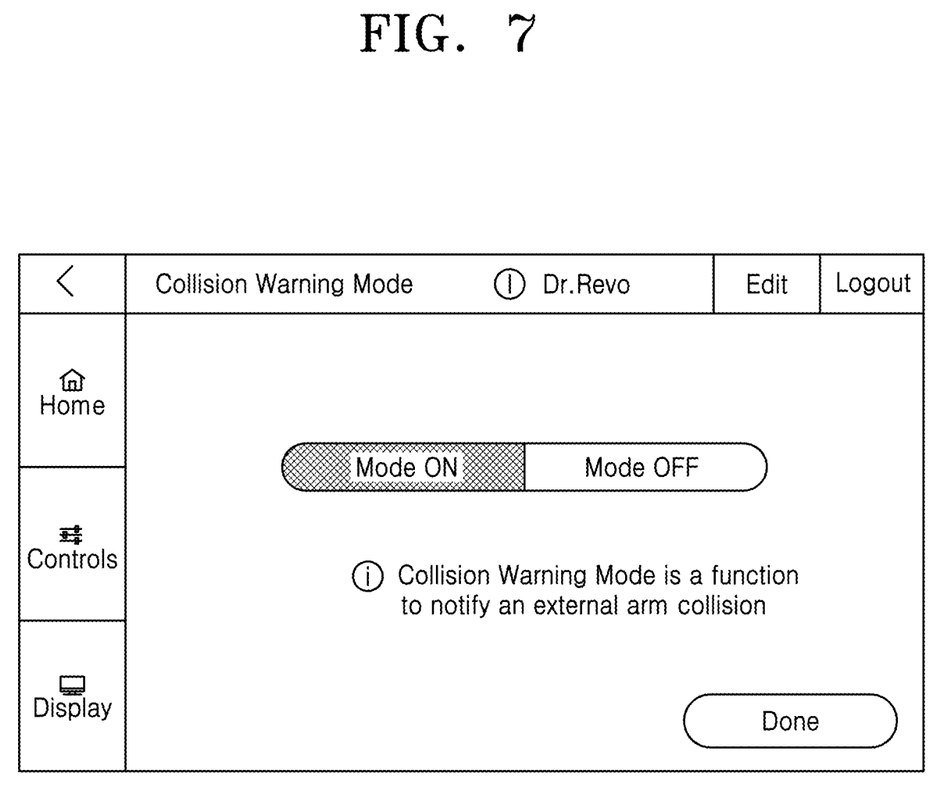
FIG. 7 is a diagram showing an example of a program for executing a method of mitigating the collision of a slave robot according to an embodiment.

FIG. 7 is a diagram showing an example of a program for executing the above-described method. A program according to an example may include Mode ON and Mode OFF functions so that a user may selectively execute the program. When the user sets the program to be Mode ON, automatic control may be performed to mitigate the collision of the slave robot. Alternatively, when the user sets the program to be Mode OFF, the control function for mitigating the collision of the slave robot may not be performed. Besides, the program according to an example may include a setting function for executing the above method, e.g., for setting an alarm output method.

In addition, the structure of the data used in the above-described method may be recorded on a computer-readable recording medium through various means. Examples of the computer readable recording medium include magnetic storage media (e.g., ROM, RAM, USB, floppy disks, hard disks, etc.), optical recording media (e.g., CD-ROMs, DVDs, etc.), etc.

While the embodiments of the disclosure have been described in detail, it is to be understood that the disclosure is not limited to the disclosed embodiments of the disclosure, but, on the contrary, is intended to cover various modifications and equivalent arrangements included within the spirit and scope of the appended claims.

INDUSTRIAL APPLICABILITY

According to an embodiment of the present disclosure, a method of reducing collision of a slave robot for surgery may be applied to robot devices that may be used in various industries. The method may be applied to various types of robot devices and robot systems, e.g., industrial robots, medical robots, mobile robots, etc.

The invention claimed is:

1. A method of mitigating a collision of a slave robot for surgery, the method comprising:
   first obtaining an external torque generated in response to the slave robot colliding with another object or a person;
   second obtaining a joint angle of the slave robot;
   calculating a target joint angle for changing a position of the slave robot based on the obtained external torque and the obtained joint angle, such that the external torque is attenuated;
   controlling the slave robot to change the position thereof from the obtained joint angle to the calculated target joint angle;
   comparing the obtained external torque with a reference value;
   repeatedly performing a cycle of the first obtaining, second obtaining, calculating, controlling and comparing, in response to the obtained external torque being equal to or greater than the reference value;
   measuring a period in which the cycle is repeatedly performed; and
   controlling the slave robot not to move in response to the measured period being equal to or longer than a preset period.

2. The method of claim 1, wherein the first obtaining comprises:
   measuring, by a torque sensor, a torque of a motor installed in the slave robot; and
   calculating the external torque from the measured torque of the motor.

3. The method of claim 2, wherein the first obtaining comprises:
   measuring, by a current sensor, a current flowing through the motor installed in the slave robot; and
   calculating the external torque from the measured current value.

4. The method of claim 3, wherein the calculating of the external torque from the measured current value comprises:
   calculating the torque of the motor from the measured current value by using a proportionality between the torque of the motor and the current of the motor;
   calculating a gravity compensation torque for compensating for a gravity applied to the slave robot; and
   calculating the external torque based on the calculated torque of the motor and the calculated gravity compensation torque.

5. The method of claim 1, wherein the target joint angle is calculated by a linear combination of the obtained external torque and the obtained joint angle.

6. The method of claim 1, further comprising outputting an alarm to notify an operator of the slave robot colliding with another object or person.

7. The method of claim 6, wherein the alarm comprises at least one of a visual alarm, an audible alarm, or a tactile alarm.

8. The method of claim 1, wherein the slave robot is remotely controlled according to a command of an operator, which is an input through a master console.

9. A robot system for surgery, the robot system comprising:
   a master console configured to be operated by an operator;
   a slave robot configured to move based on a manipulation on the master console; and
   at least one processor configured to control a movement of the slave robot such that a collision between the slave robot and another object or person is weakened, the at least one processor further configured to:
   first obtain an external torque that is generated in response to the slave robot colliding with another object or person;
   second obtain a joint angle of the slave robot;
   calculate a target joint angle for changing a position of the slave robot based on the obtained external torque and the obtained joint angle, such that the external torque is attenuated;
   control the slave robot to change the position thereof from the obtained joint angle to the calculated target joint angle;
   compare the obtained external torque with a reference value;

repeatedly perform a cycle of the first obtaining, second obtaining, calculating, controlling and comparing, in response to the obtained external torque being equal to or greater than the reference value;

measure a period in which the cycle is repeatedly performed; and control the slave robot not to move in response to the measured period being equal to or longer than a preset period.

10. A non-transitory computer recording medium storing instructions to perform a method of mitigating a collision of a slave robot for surgery, the method comprising:

first obtaining an external torque generated in response to the slave robot colliding with another object or a person;

second obtaining a joint angle of the slave robot;

calculating a target joint angle for changing a position of the slave robot based on the obtained external torque and the obtained joint angle, such that the external torque is attenuated;

controlling the slave robot to change the position thereof from the obtained joint angle to the calculated target joint angle;

comparing the obtained external torque with a reference value;

repeatedly performing a cycle of the first obtaining, second obtaining, calculating, controlling and comparing, in response to the obtained external torque being equal to or greater than the reference value;

measuring a period in which the cycle is repeatedly performed; and controlling the slave robot not to move in response to the measured period being equal to or longer than a preset period.

* * * * *